(12) United States Patent
Stefani et al.

(10) Patent No.: US 9,138,536 B2
(45) Date of Patent: Sep. 22, 2015

(54) APPARATUS AND A METHOD FOR MONITORING A VASCULAR ACCESS

(75) Inventors: David Stefani, Modena (IT); Carlo Alberto Lodi, Carpi (IT); Salvatore Sanna, Mirandola (IT)

(73) Assignee: Gambro Lundia AB, Lund (SE)

( * ) Notice: Subject to any disclaimer, the term of this patent is extended or adjusted under 35 U.S.C. 154(b) by 602 days.

(21) Appl. No.: 12/935,672

(22) PCT Filed: Apr. 1, 2008

(86) PCT No.: PCT/IB2008/000768
§ 371 (c)(1),
(2), (4) Date: Nov. 5, 2010

(87) PCT Pub. No.: WO2009/122229
PCT Pub. Date: Oct. 8, 2009

(65) Prior Publication Data
US 2011/0046533 A1    Feb. 24, 2011

(51) Int. Cl.
| | |
|---|---|
| *A61M 1/00* | (2006.01) |
| *A61M 31/00* | (2006.01) |
| *A61B 5/00* | (2006.01) |
| *A61M 5/168* | (2006.01) |
| *A61M 37/00* | (2006.01) |
| *A61M 1/36* | (2006.01) |

(52) U.S. Cl.
CPC ......... *A61M 5/16836* (2013.01); *A61M 1/3656* (2014.02); *A61M 5/16859* (2013.01); *A61M 1/3653* (2013.01); *A61M 1/3669* (2013.01); *A61M 2205/15* (2013.01); *A61M 2205/3306* (2013.01); *A61M 2205/3375* (2013.01)

(58) Field of Classification Search
USPC ................. 600/301, 407, 473, 476, 477, 547; 604/4.01, 4.02, 5.01–5.05, 93.01, 6.05, 604/6.06, 6.09, 6.11; 210/645, 646, 739, 210/741, 745
See application file for complete search history.

(56) References Cited

U.S. PATENT DOCUMENTS

| | | |
|---|---|---|
| 3,618,602 A | 11/1971 | Shaw |
| 3,864,676 A | 2/1975 | Macias et al. |
| 4,010,749 A | 3/1977 | Shaw |
| 4,181,610 A | 1/1980 | Shintani et al. |

(Continued)

FOREIGN PATENT DOCUMENTS

| | | |
|---|---|---|
| CA | 2 175 903 | 5/1995 |
| CA | 2 282 628 | 11/2006 |

(Continued)

OTHER PUBLICATIONS

Canadian Office Action issued Jul. 11, 2012, for corresponding Canadian Appln. No. 2,673,574.

(Continued)

*Primary Examiner* — Tan-Uyen (Jackie) T Ho
*Assistant Examiner* — Mark Wardas
(74) *Attorney, Agent, or Firm* — K&L Gates LLP

(57) ABSTRACT

An apparatus for monitoring a vascular access includes a dialysis circuit having a venous needle and a blood pump of a peristaltic type which generates oscillatory perturbations in the circuit. An optical sensor, arranged on a patient's body by the venous needle, perceives the perturbations transmitted through the needle and sends a pulsating signal to an analysis device. The absence of a pulsating signal indicates a detachment of the needle.

51 Claims, 6 Drawing Sheets

(56) References Cited

U.S. PATENT DOCUMENTS

| | | | |
|---|---|---|---|
| 4,194,974 A | | 3/1980 | Jonsson |
| 4,294,263 A | | 10/1981 | Hochman |
| 4,295,475 A | | 10/1981 | Torzala |
| 4,399,823 A | | 8/1983 | Donnelly |
| 4,399,824 A | | 8/1983 | Davidson |
| 4,416,595 A | * | 11/1983 | Cromie .......... 417/476 |
| 4,501,583 A | | 2/1985 | Troutner |
| 4,534,756 A | | 8/1985 | Nelson |
| 4,648,869 A | | 3/1987 | Bobo, Jr. |
| 4,661,096 A | | 4/1987 | Teeple |
| 4,703,758 A | * | 11/1987 | Omura .......... 600/485 |
| 4,710,163 A | | 12/1987 | Butterfield |
| 4,846,792 A | | 7/1989 | Bobo et al. |
| 4,877,034 A | | 10/1989 | Atkins et al. |
| 4,898,576 A | | 2/1990 | Philip |
| 5,026,348 A | | 6/1991 | Venegas |
| 5,087,245 A | * | 2/1992 | Doan .......... 604/67 |
| 5,100,374 A | | 3/1992 | Kageyama |
| 5,139,482 A | | 8/1992 | Simeon et al. |
| 5,211,201 A | | 5/1993 | Kamen et al. |
| 5,454,374 A | | 10/1995 | Omachi |
| 5,509,822 A | | 4/1996 | Negus et al. |
| 5,674,390 A | | 10/1997 | Matthews et al. |
| 5,709,670 A | | 1/1998 | Vancaillie et al. |
| 5,718,692 A | | 2/1998 | Schon et al. |
| 5,730,418 A | | 3/1998 | Feith et al. |
| 5,779,657 A | | 7/1998 | Daneshvar |
| 5,803,915 A | | 9/1998 | Kremenchugsky et al. |
| 5,813,432 A | | 9/1998 | Elsdon et al. |
| 5,911,706 A | | 6/1999 | Estabrook et al. |
| 5,931,801 A | | 8/1999 | Burbank et al. |
| 5,954,691 A | | 9/1999 | Prosl |
| 6,009,339 A | | 12/1999 | Bentsen et al. |
| 6,038,914 A | | 3/2000 | Carr et al. |
| 6,044,691 A | | 4/2000 | Kenley et al. |
| 6,077,443 A | * | 6/2000 | Goldau .......... 210/741 |
| 6,090,048 A | | 7/2000 | Hertz et al. |
| 6,167,765 B1 | | 1/2001 | Weitzel |
| 6,206,851 B1 | | 3/2001 | Prosl |
| 6,208,880 B1 | | 3/2001 | Bentsen et al. |
| 6,221,040 B1 | | 4/2001 | Kleinekofort |
| 6,397,661 B1 | | 6/2002 | Grimes et al. |
| 6,402,207 B1 | | 6/2002 | Segal et al. |
| 6,406,460 B1 | | 6/2002 | Hogan |
| 6,461,329 B1 | | 10/2002 | Van Antwerp et al. |
| 6,500,154 B1 | | 12/2002 | Hakky et al. |
| 6,565,525 B1 | | 5/2003 | Burbank et al. |
| 6,572,576 B2 | | 6/2003 | Brugger et al. |
| 6,575,927 B1 | | 6/2003 | Weitzel et al. |
| 6,582,397 B2 | | 6/2003 | Alesi et al. |
| 6,585,675 B1 | | 7/2003 | O'Mahony et al. |
| 6,595,942 B2 | | 7/2003 | Kleinekofort |
| 6,612,624 B1 | | 9/2003 | Segal et al. |
| 6,623,443 B1 | | 9/2003 | Polaschegg |
| 6,663,585 B1 | | 12/2003 | Ender |
| 6,752,785 B2 | | 6/2004 | Van Antwerp et al. |
| 6,827,698 B1 | | 12/2004 | Kleinekofort |
| 6,924,733 B1 | | 8/2005 | McTier et al. |
| 6,932,786 B2 | | 8/2005 | Giacomelli et al. |
| 6,979,306 B2 | | 12/2005 | Moll |
| 7,022,098 B2 | | 4/2006 | Wariar et al. |
| 7,040,142 B2 | | 5/2006 | Burbank |
| 7,052,480 B2 | | 5/2006 | Han et al. |
| 7,053,781 B1 | | 5/2006 | Haire et al. |
| 7,056,316 B1 | | 6/2006 | Burbank et al. |
| 7,060,047 B2 | | 6/2006 | Lodi et al. |
| 7,070,591 B2 | | 7/2006 | Adams et al. |
| 7,087,033 B2 | | 8/2006 | Brugger et al. |
| 7,276,041 B2 | | 10/2007 | Moll |
| 7,729,735 B1 | * | 6/2010 | Burchman .......... 600/339 |
| 7,824,355 B2 | * | 11/2010 | Langley et al. .......... 604/4.01 |
| 7,826,890 B1 | * | 11/2010 | Winchester et al. .......... 600/477 |
| 8,251,941 B2 | * | 8/2012 | Humes et al. .......... 604/6.03 |
| 8,376,978 B2 | | 2/2013 | Roger et al. |
| 2002/0198483 A1 | | 12/2002 | Warlar et al. |
| 2003/0009123 A1 | | 1/2003 | Brugger et al. |
| 2003/0036719 A1 | | 2/2003 | Giacomelli et al. |
| 2003/0126910 A1 | | 7/2003 | Burbank |
| 2003/0128125 A1 | * | 7/2003 | Burbank et al. .......... 340/605 |
| 2003/0128126 A1 | | 7/2003 | Burbank et al. |
| 2003/0152482 A1 | | 8/2003 | O'Mahony et al. |
| 2003/0176829 A1 | | 9/2003 | Lodi et al. |
| 2003/0194894 A1 | | 10/2003 | Wariar et al. |
| 2003/0195453 A1 | | 10/2003 | Han et al. |
| 2003/0195454 A1 | | 10/2003 | Wariar et al. |
| 2004/0054352 A1 | | 3/2004 | Adams et al. |
| 2004/0113801 A1 | | 6/2004 | Gustafson et al. |
| 2004/0185709 A1 | | 9/2004 | Williams, Jr. et al. |
| 2004/0186409 A1 | | 9/2004 | Cavalcanti et al. |
| 2004/0186415 A1 | | 9/2004 | Burbank et al. |
| 2004/0201216 A1 | | 10/2004 | Segal et al. |
| 2004/0243046 A1 | | 12/2004 | Brugger et al. |
| 2005/0010118 A1 | | 1/2005 | Toyoda et al. |
| 2005/0010157 A1 | | 1/2005 | Baraldi et al. |
| 2005/0038325 A1 | | 2/2005 | Moll |
| 2005/0096578 A1 | | 5/2005 | Kleinekofort |
| 2005/0131332 A1 | | 6/2005 | Kelly et al. |
| 2005/0230313 A1 | | 10/2005 | O'Mahony et al. |
| 2005/0241387 A1 | | 11/2005 | Miesel et al. |
| 2005/0245858 A1 | | 11/2005 | Miesel et al. |
| 2005/0256451 A1 | | 11/2005 | Adams et al. |
| 2006/0012774 A1 | | 1/2006 | O'Mahony et al. |
| 2006/0069339 A1 | | 3/2006 | Moll |
| 2006/0081517 A1 | | 4/2006 | Toyoda et al. |
| 2006/0087120 A1 | | 4/2006 | Segal et al. |
| 2006/0116623 A1 | | 6/2006 | Han et al. |
| 2006/0130591 A1 | | 6/2006 | Perkins |
| 2006/0166548 A1 | | 7/2006 | Williams, Jr. et al. |
| 2006/0184087 A1 | | 8/2006 | Wariar et al. |
| 2007/0118064 A1 | | 5/2007 | Ueda et al. |
| 2007/0265533 A1 | * | 11/2007 | Tran .......... 600/481 |
| 2008/0041792 A1 | | 2/2008 | Crnkovich et al. |
| 2008/0195021 A1 | * | 8/2008 | Roger et al. .......... 604/4.01 |

FOREIGN PATENT DOCUMENTS

| | | |
|---|---|---|
| CA | 2 660 537 | 2/2009 |
| DE | 4014572 | 11/1991 |
| DE | 19802985 | 7/1999 |
| DE | 10 2006 041 265 B3 | 12/2007 |
| EP | 0 328 162 A2 | 8/1989 |
| EP | 0 259 551 | 9/1990 |
| EP | 0 472 798 | 3/1994 |
| EP | 1 263 488 B1 | 12/2002 |
| EP | 1 401 518 | 3/2006 |
| EP | 1 736 185 A2 | 12/2006 |
| FR | 2 737 124 | 1/1997 |
| GB | 2207749 | 2/1989 |
| JP | 01250733 | 10/1989 |
| JP | 4-33860 | 4/1992 |
| JP | 2000131286 | 5/2000 |
| JP | 2001517469 | 10/2001 |
| JP | 2006055588 | 3/2006 |
| JP | 2006110118 | 4/2006 |
| JP | 2007020738 | 2/2007 |
| JP | 2007502148 | 2/2007 |
| JP | 2007143895 | 6/2007 |
| JP | 200800219 | 1/2008 |
| JP | 2008503318 | 2/2008 |
| WO | WO 81/00295 | 2/1981 |
| WO | WO 89/12228 | 12/1989 |
| WO | WO 95/12545 | 5/1995 |
| WO | WO 97/03712 | 2/1997 |
| WO | WO 97/10013 | 3/1997 |
| WO | WO 98/38485 | 9/1998 |
| WO | WO 99/12588 | 3/1999 |
| WO | WO 99/24145 | 5/1999 |
| WO | WO 99/29356 | 6/1999 |
| WO | WO 01/47581 | 7/2001 |
| WO | WO 01/47581 A1 | 7/2001 |
| WO | WO 02/102441 A1 | 12/2002 |
| WO | WO 03/000315 | 1/2003 |
| WO | WO 03/002174 | 1/2003 |
| WO | WO 03/006944 | 1/2003 |

(56) References Cited

FOREIGN PATENT DOCUMENTS

| WO | WO 03/086504 | 10/2003 |
|---|---|---|
| WO | WO 03/086504 A2 | 10/2003 |
| WO | WO 03/086505 | 10/2003 |
| WO | WO 03/086506 | 10/2003 |
| WO | WO 2004/040369 | 5/2004 |
| WO | WO 2004/082740 | 9/2004 |
| WO | WO 2004/084972 | 10/2004 |
| WO | WO 2004/108192 | 12/2004 |
| WO | WO 2005/019416 | 3/2005 |
| WO | WO 2005/046439 | 5/2005 |
| WO | WO 2005/105199 | 11/2005 |
| WO | WO 2005/105200 | 11/2005 |
| WO | WO 2006/001759 | 1/2006 |
| WO | WO 2006/001759 A1 | 1/2006 |
| WO | WO 2006/030320 | 3/2006 |
| WO | WO 2006/085220 | 8/2006 |
| WO | WO 2006/138359 A2 | 12/2006 |
| WO | WO 2007/033025 A2 | 3/2007 |
| WO | WO 2008/021462 | 2/2008 |

OTHER PUBLICATIONS

Japanese Office Action issued Sep. 10, 2012 for corresponding Japanese Appln. No. 2009-549156.
Japanese Office Action mailed Mar. 13, 2014 for corresponding Japanese Appln. No. 2013-001720.
Japanese Office Action mailed Nov. 27, 2013 for corresponding Japanese Appln. No. 2013-001720.
International Search Report mailed Jul. 15, 2008 for corresponding Intl. Appln. No. PCT/US2008/051260.
International Search Report and Written Opinion mailed Apr. 18, 2007 for corresponding Intl. Appln. No. PCT/IB2006/003074.
Takei et al., "New advanced BARC and gap fill materials based on sublimate reduction for 193nm lithography", Advances in Resist Technology and Processing XXIII, Proc. of SPIE, vol. 6153, 2006 (10 pages).
Trefonas et al., "Orgranic Antireflective Coatings for 193nm Lithography", Proc. of SPIE, vol. 3678, Mar. 1999 (11 pages).
Xu et al., "New Antreflective Coatings for 193 nm Lithography", Proc. of SPIE, vol. 3333.

\* cited by examiner

APPARATUS AND A METHOD FOR MONITORING A VASCULAR ACCESS

CROSS REFERENCE TO RELATED APPLICATIONS

This application is a national phase application based on PCT/IB2008/000768 filed Apr. 1, 2008, which is incorporated herein by reference, and claims the benefit thereof

BACKGROUND OF THE INVENTION

The invention relates to an apparatus and a method for monitoring a vascular access.

Specifically, though not exclusively, the invention can be usefully applied in detection of detachment of a needle in an extracorporeal blood circuit, such as for example an extracorporeal circuit used in a dialysis treatment.

The prior art comprises various systems for monitoring a needle, typically a needle (generally called a venous needle) via which extracorporeal blood is returned to the body of the individual.

Some known systems for detecting a detachment of the needle from the patient are based on detection of the presence of blood that has exited from the detached needle and/or the vascular access and spilled onto the patient's body. These systems can be based on a monitoring performed with a sensor of an electrical parameter (such as for example in US 2002/0198483, WO 99/24145, FR 2737124, U.S. Pat. No. 7,276,041), or an optical parameter (such as for example WO 2006/001759 and US 2006/0130591), or both (such as for example EP 1736185 and EP 1263488).

Other known systems (see for example U.S. Pat. No. 6,663,585, WO 02/102441, WO 01/47581, WO 03/086504, WO 2006/138359, US 2006/0081517, DE 102006041265) are based on monitoring the state of an electrical circuit formed at least partly by at least a tract of blood circuit, exploiting blood's characteristic of being electrically conductive.

A further known system is described in US 2007/0118064, in which an apparatus guides the blood in the venous line in an inverse direction, using an ultrafiltration pump, and detects a detachment of the venous needle on the basis of recognition of a presence of air bubbles in the venous line itself.

There also exist systems based on the monitoring of the pressure in the extracorporeal circuit, such as for example U.S. Pat. No. 4,898,576, EP 328162, US 2005/0010118, U.S. Pat. No. 6,077,443, U.S. Pat. No. 6,221,040, WO 03/002174, U.S. Pat. No. 6,090,048.

U.S. Pat. No. 4,898,576 describes an infusion system in which the infusion flow has a periodic variation and in which the state of the vascular axis is determined on the basis of the flow resistance, which is calculated on the basis of the variation in pressure in relation to the flow variation.

EP 328162 describes an infusion system in which the pressure signal measured in the infusion line downstream of the infusion pump is filtered by a high-pass filter and the filtered signal is evaluated in order to calculate the correct communication with the vascular access.

US 2005/0010118 describes a dialysis apparatus in which the disconnection of the needle from the vascular access is detected when the frequency component, caused by the heartbeat of the patient, disappears from the pressure signal measured in the extracorporeal circuit.

U.S. Pat. No. 6,077,443 shows a dialysis apparatus in which a series of pressure pulses are generated in the dialysis circuit and the detachment of the needle is detected by the monitoring of the pressure pulses induced in the extracorporeal blood circuit of the series of pulses.

U.S. Pat. No. 6,221,040 shows a dialysis apparatus in which the detachment of the venous needle is detected by analyzing both the venous pressure and the arterial pressure of the extracorporeal circuit.

WO 03/002174 describes a dialysis apparatus in which the detachment of the venous needle is detected if both the venous pressure and the arterial pressure are reduced and, during the same period of time, the extracorporeal blood flow stays constant.

U.S. Pat. No. 6,090,048 describes a dialysis apparatus in which the detachment of the venous needle from the patient is determined by verifying whether a pressure wave, generated by the blood pump or the heartbeat, passes through the needle and reaches the pressure sensor on the venous line.

The prior art also comprises WO 2007/033025 which describes an apparatus infusion control in which the infusion fluid flow rate is controlled in response to patient parameter values measured, such as for example pulse oximetry and blood pressure.

SUMMARY OF THE INVENTION

An aim of the present invention is to provide a way of determining a detachment of a needle from the vascular access of an individual.

An advantage of the invention is to realize a simple, economical and reliable system for detecting, in good time, a detachment of a needle, in particular the venous needle in an extracorporeal blood circuit.

A further advantage of the invention is to provide a method and an apparatus for detecting detachment of a needle by means of a relatively low-cost simple instrumentation.

A further advantage is to make available a method and an apparatus which can discriminate between the effective detachment of the needle and the occurrence of other non-alarming facts, such as for example displacement of the individual (perhaps during a dialysis treatment a patient might move his or her arm which the vascular access is realised in), variations of velocity/frequency of the blood pump, etc.

These aims and more besides are all attained by the invention as it is characterised in one or more of the appended claims.

In a specific embodiment of the invention, the detachment of the needle from the vascular access is determined by means of a method and/or an apparatus configured to perform the monitoring of the power spectrum of the vascular pulsation of the individual in proximity of the needle. In particular this monitoring comprises verifying, either continuously or periodically, the presence or not, in the vascular pulsation of the individual, of the contribution due to the pulsation which is induced in the extracorporeal system by an actuator predisposed to generate pulses (such as for example a peristaltic pump which generates pulses during normal functioning thereof).

In a specific embodiment of the invention, an apparatus and/or a method for determining the detachment of a needle comprises means for and/or a step of monitoring the energy of a signal deriving from the vascular pulsation in proximity of the needle, and control means for and/or a step of verifying a variation of the energy.

In a specific embodiment of the invention, an apparatus and/or a method for determining detachment of a needle comprises means for and/or a step of monitoring a signal indicating the vascular pulsation in proximity of the needle, and control means for and/or a step of verifying a variation of the signal.

In particular the control means can comprise means for filtering the signal which filter the signal in a range (of predetermined entity) around the—known—frequency of a pulse generator operating in the extracorporeal fluid system. The control means can be predisposed to perform a frequency analysis of the signal received from the means for monitoring.

In particular the above-cited means for monitoring can comprise a radiation sensor (for example optical or sound radiations) which is operatively associated to the body of the individual in proximity of the needle. The sensor can be, for example, configured for detection of radiation absorbed and/or reflected. The sensor can be, in particular, a pulse oximeter predisposed in proximity of the needle, for example a pulse oximeter applied to a fingertip of a hand of the arm the vascular access is realised in.

In particular the above-cited means for monitoring and controlling operate on the basis of the monitoring and processing of signals by frequency analysis of the signals themselves. This makes an accurate measuring of the absolute value of the signals themselves not strictly necessary.

In particular the means for monitoring and controlling perform a verification of the absence (or reduction below a predetermined threshold) of a certain component of the monitored signal, in particular a pulsating or undulating component of known frequency.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The following description will be made with reference to the accompanying figures of the drawings, provided by way of non-limiting example.

DETAILED DESCRIPTION

Figure 1:
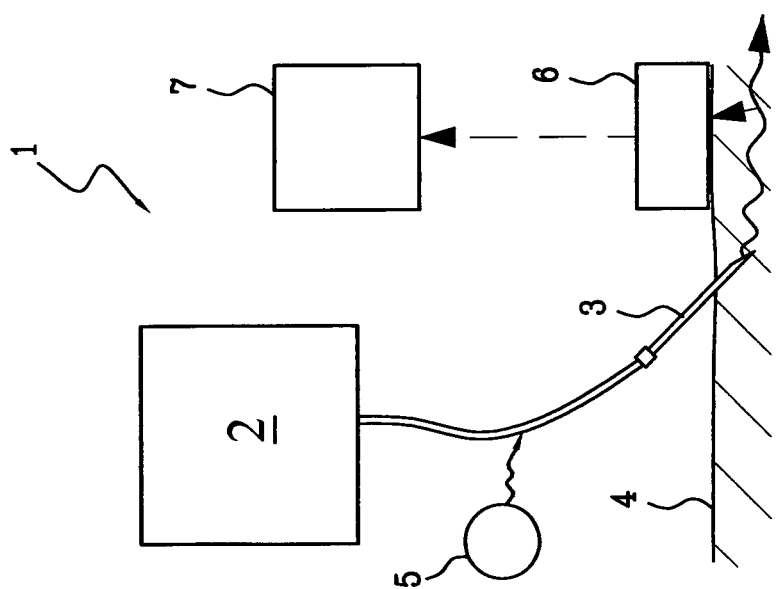
FIG. 1 is a schematic representation of a first embodiment of a monitoring apparatus according to the present invention, in which the monitoring apparatus is operatively associated to a fluid infusion system (for example a medical fluid or a corporeal fluid) into the vascular system of an individual.

With reference to FIG. 1, 1 denotes in its entirety an apparatus for monitoring a vascular access, 2 denotes a fluid transport system for moving a fluid, 3 a needle connected at an end thereof to the fluid transport system and an opposite end thereof to a vascular access of an individual, 4 the body of the individual, 5 a perturbation generator for generating perturbations in the fluid transport system, 6 a sensor configured to be operatively associated to the body 4 of the individual for emitting a signal indicating the pertumbations which are induced in the transport system 2 by the generator 5 and which are transmitted into the body 4 of the individual via the needle 3, 7 an analysis device configured to recognise a determined situation, which can be traced to the detachment of the needle 3 from the vascular access, on the basis of the signal received from the sensor 6. The determined situation can be, for example, the absence or drastic reduction of the perturbations originating from the generator 5.

Optionally the generator 5 can be predisposed to generate variations of at least a parameter in the fluid transport system 2. The generator 5 can optionally be predisposed to generate variations of at least a parameter associated to the needle 3 (in particular a characteristic parameter of the fluid path defined internally of the needle). The generator 5 can optionally be predisposed to generate variations of at least a parameter both in the fluid transport system 2 and in the needle 3.

The generator 5 can be predisposed to operate directly on the fluid transport system 2, having at least a part associated directly to the system 2 (for example in direct contact with a part of the system 2, the part possibly comprising, for example, a wall delimiting a fluid path internal of the system 2). The generator 5 can be, alternatively or in addition to the aforementioned, predisposed to operate directly on the needle 3, having at least a part thereof associated directly to the needle 3 or to the fluid path defined internally of the needle 3.

The analysis device 7 can optionally be connected to the fluid transport system 2 (for example to a control unit which governs the system itself) for receiving and/or supplying the system 2 such that, from an analysis of the data available both to the analysis device 7 and to the transport system 2, it is possible to calculate, with a relatively greater certainty, if the needle 3 has effectively become detached. By way of example, the analysis device 7 and the transport system 2 can be connected such as to determine whether, coincidentally with the recognition of a determined and potentially faulty situation on the part of the analysis device 7, there is also present at least a further situation under the control of the transport system 2 such as, for example, the operativity of the perturbation generator 5. In this case, if both the conditions are shown to exist, one being potentially faulty signalled by the device 7 and the other of the generator 5 activity, an alarm situation can be set off (for example by the analysis device 7 and/or by the transport system 2). There can also be other situations under the control of the transport system 2 which are used, in combination with what is detected by the analysis device 7, to determine an alarm situation or in any case a faulty situation, such as for example reaching of a determined pressure level (or hematocrit level in the case of blood transport, or concentration level of a determined substance, or particle, or element in the transported fluid) in a determined zone of the transport system 2, the halting of the fluid movement along the system etc. All the above-mentioned various situations controlled by the transport system 2 can be used (in combination with the potentially faulty system detected by the device 7) by themselves or in combination with one another.

Figure 2:
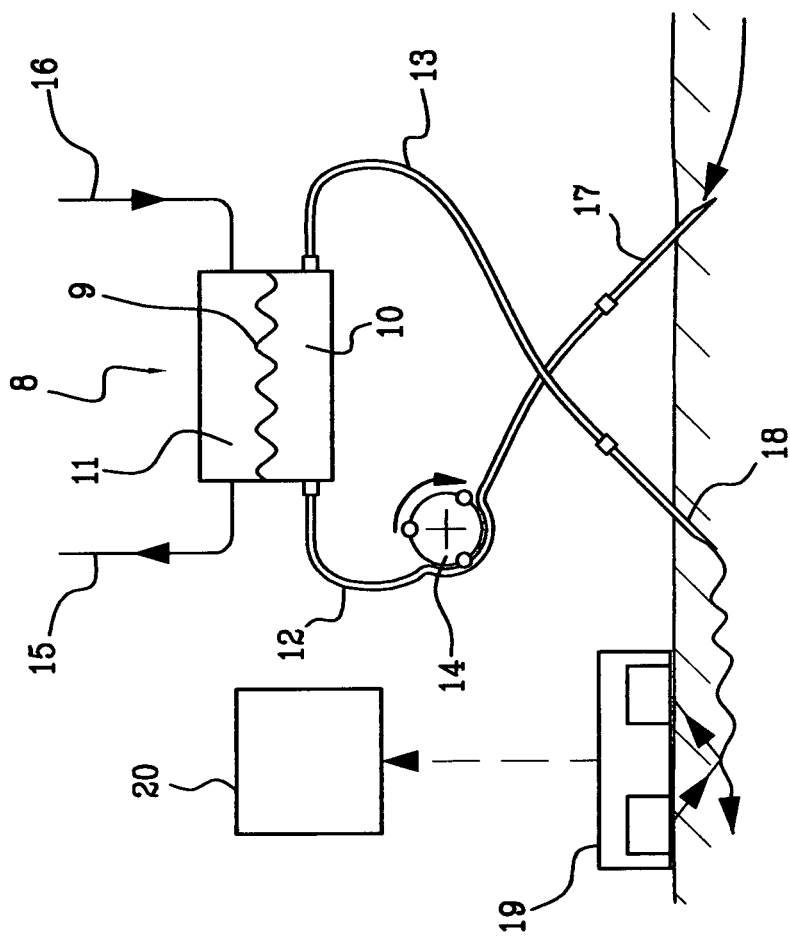
FIG. 2 shows a second embodiment of a monitoring apparatus of the present invention, in which the monitoring apparatus is operatively associated to an extracorporeal treatment system of the blood of an individual (a patient or a donor) with an extracorporeal circuit of the double-needle type.

With reference to FIG. 2, 8 denotes a membrane exchanger for extracorporeal blood treatment, provided with a semipermeable membrane 9 which separates a blood chamber 10 from a fluid chamber 11, 12 being a blood removal line (arterial line) for transport of blood from a vascular access of an individual to an inlet of the blood chamber 10, 13 denoting a blood return line (venous line) for returning the treated blood from an outlet of the blood chamber 10 to the vascular access of the individual, 14 denoting a blood pump (in the present embodiment a rotary peristaltic pump) for blood circulation in the extracorporeal circuit, 15 denoting a discharge line for fluid drainage from the fluid chamber 11, 16 denoting a treatment fluid (dialysate) supply line to the fluid chamber 11, 17 a blood removal needle (arterial needle) connected to the removal line 12, 18 a blood return needle (venous needle) connected to the blood return line 13, 19 a sensor (in the present case a radiation reflecting type, for example light or sound radiation) configured for emitting a signal indicating the perturbations which are induced in the extracorporeal blood circuit by the blood pump 14 and which are transmitted into the body of the individual via the venous needle 18, 20 being a control unit which is predisposed to govern the functioning of the apparatus for the treatment of the extracorporeal blood and which is provided with an analysis device for recognising detachment of the venous needle 18 on the evidence of the signal received from the sensor 19.

Figure 3:
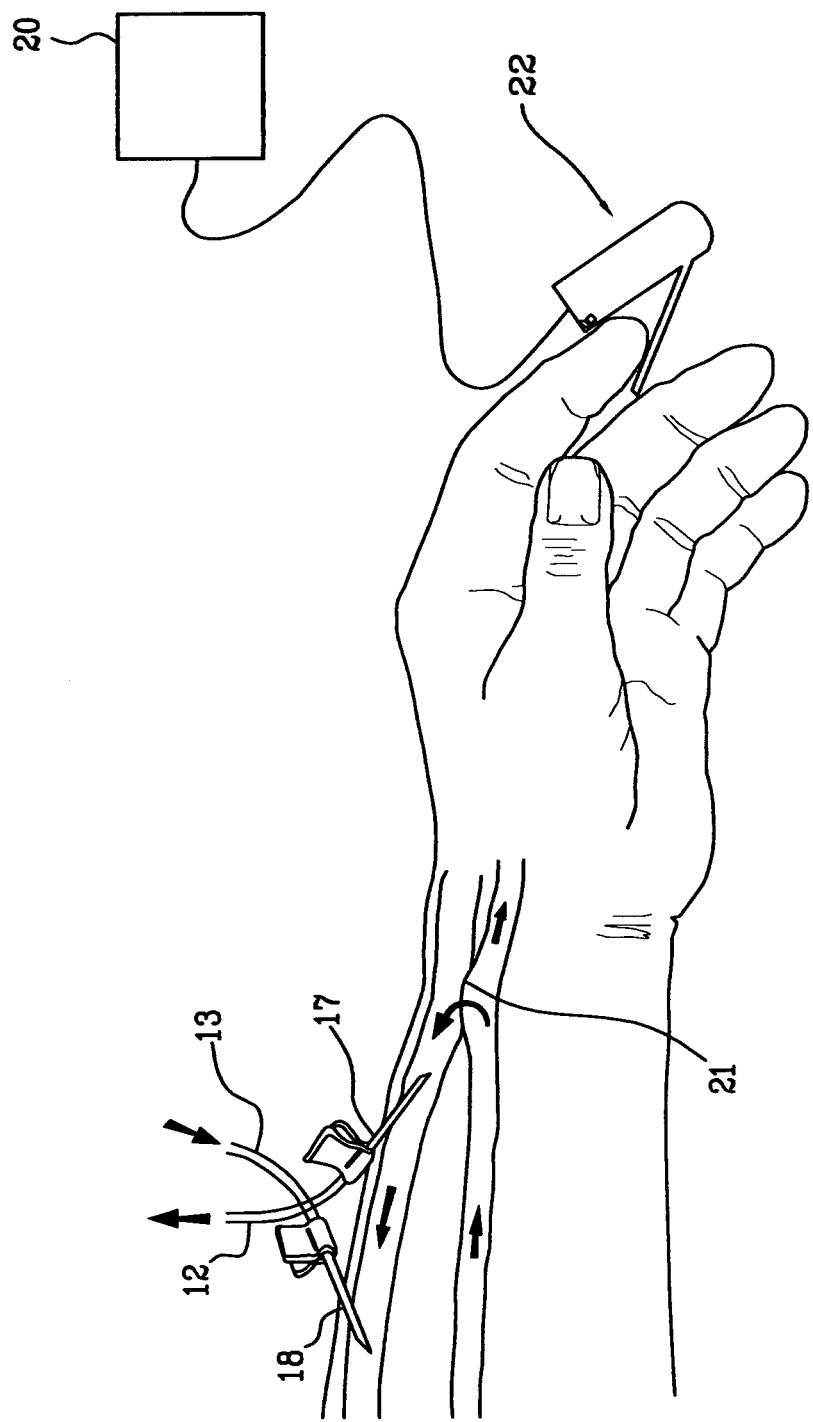
FIG. 3 shows a third embodiment of the invention, in which the monitoring apparatus sensor comprises a finger pulsimeter of a type that absorbs radiation, which is arranged such as to be very highly sensitive to pulsations induced by the blood pump on the arterial branch of a double-needle extracorporeal circuit.

With reference to FIG. 3, 21 denotes a fistula (a known type of vascular access) to which the extracorporeal circuit of FIG. 2 is connected (FIG. 3 illustrates only a part of the extracorporeal blood apparatus of FIG. 2, keeping the same numbering as in FIG. 2), 22 denotes a radiation-absorbing sensor (in the specific case an optical sensor, for example a finger pulsimeter) connected to the control unit 20 having the above-mentioned needle-detachment sensing device.

Figure 4:
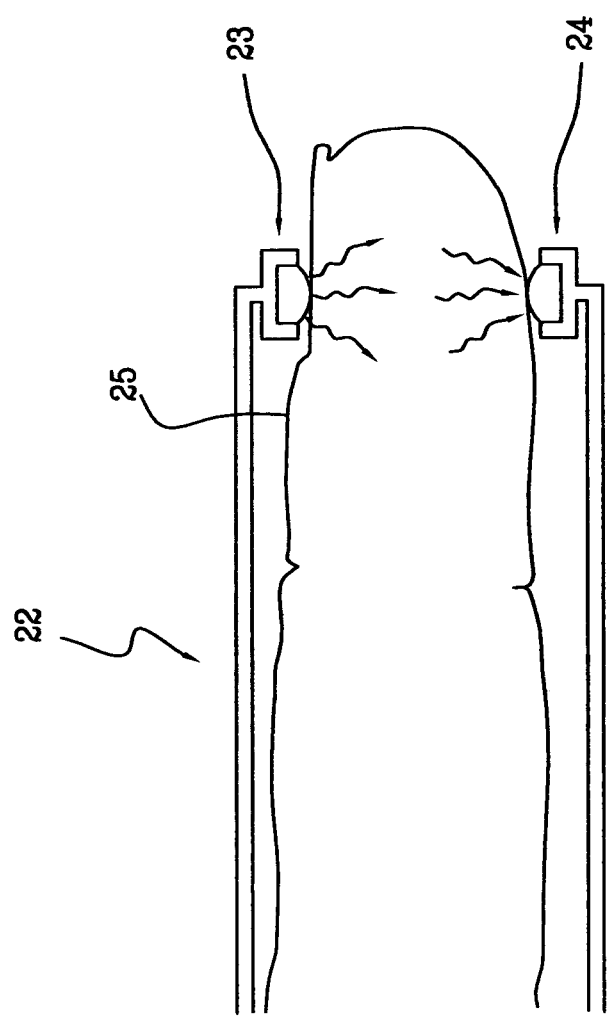
FIG. 4 is a diagram representing the functioning of an absorption pulsimeter.

With reference to FIG. 4, 23 denotes a radiation emitter (for example emitting light radiation) which is part of the sensor 22, 24 denotes a radiation receiver coupled to the emitter 23 for receiving a part of the radiations emitted by the emitter 23 which is absorbed by the tissue of the individual's body, 25 denotes the individual's body (in particular a finger) having the tissue thereof interposed between the emitter 23 and the receiver 24. In the specific case the sensor 22 comprises a pulse oximeter, of known type, in which the emitter 23 comprises, for example, a LED and the receiver 24 comprises, for example, a photo-detector. The above-mentioned pulse oximeter, in use, illuminates the individual's tissue. The light crosses the individual's body, encountering tissues, bone, skin, arterial blood and venous blood, and is thus attenuated. It is known that some elements of the individual's body (for example bone, tissue and venous blood) can absorb the light constantly, while other elements (arterial blood) can absorb the light variably according to a certain frequency. The overall signal detected by the receiver 24 is therefore a time-variable signal (pletismographic signal, see FIGS. 6 and 7). By analysing the frequency of the signal detected by the receiver 24 and sent on to the analysis device, it is possible (for example by knowing the frequency of the signal induced by the peristaltic pump or other perturbation generator and using frequency filters of known type) to recognise the contribution provided by the above-mentioned perturbation generator to the overall signal. This enables identification of any absence, or sharp reduction, in the contribution provided by the perturbation generator, and thus enables a deduction in the existence of a faulty situation (needle detachment) in the vascular access.

Figure 5:
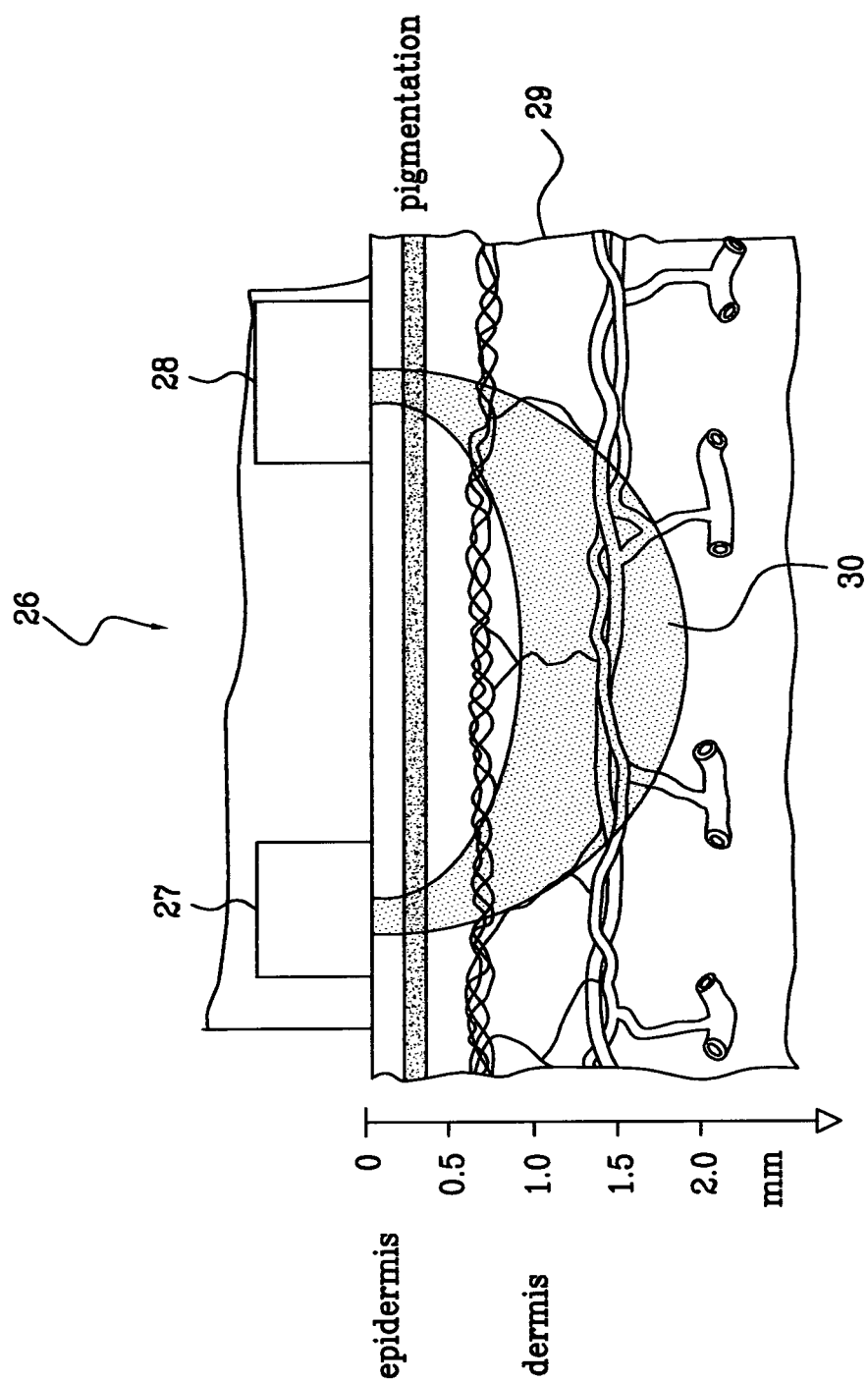
FIG. 5 is a diagram showing the functioning of a reflection pulsimeter.

With reference to FIG. 5, 26 denotes in its entirety a radiation sensor of the reflection type (usable in any one of the systems described in FIGS. 1 to 3 and located in operative connection with the analysis device 7 or with the control unit 20), 27 denotes a radiation emitter (for example light or sound radiation, 28 a receiver of reflected radiation coming from the emitter 27, 29 a tissue (for example epidermic or dermic tissue) to which the sensor 26 is frontally applied, 30 denotes the whole of the radiations which are emitted by the emitter 27 and captured by the receiver 28.

Figure 6:
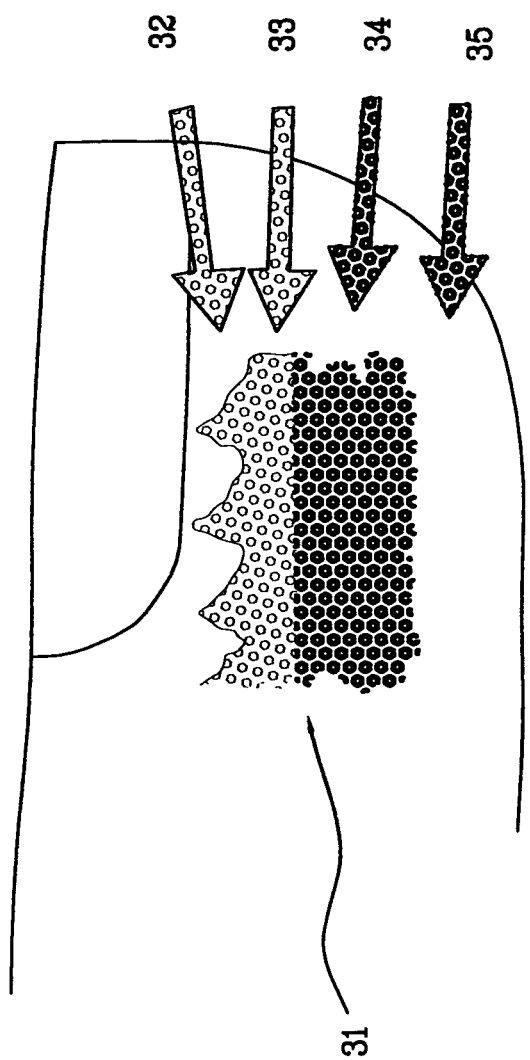
FIG. 6 is a diagram showing time progress of the radiations detected by the receiver of the pulsimeter of FIG. 4 (absorbed radiations) or FIG. 5 (reflected radiations).
Figure 7:
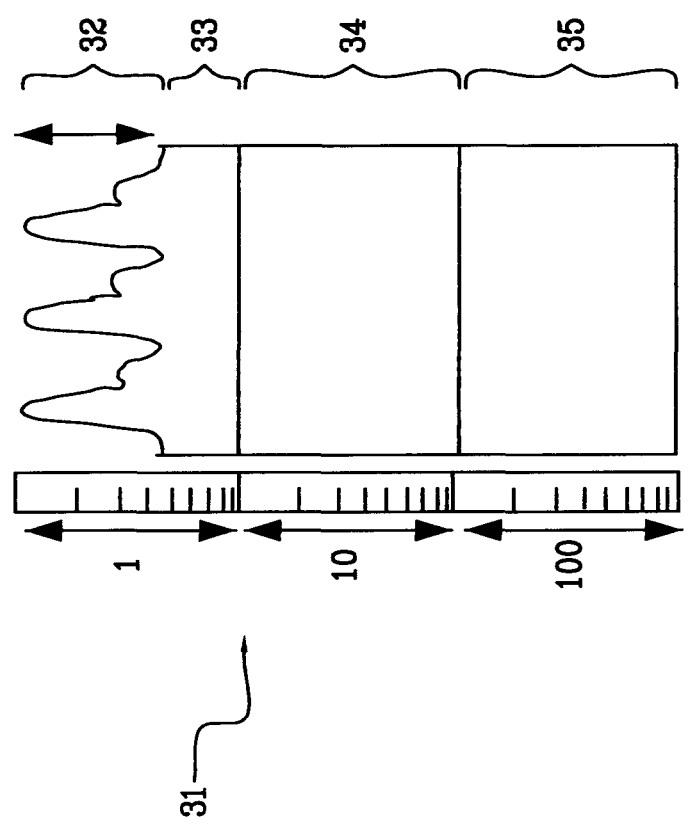
FIG. 7 schematically shows the time progress of the signal emitted by the sensor of FIG. 4 or FIG. 5.

With reference to FIG. 6, 31 denotes a graph (pletismographic signal) representing the size, in function of the time, of the absorbed radiations received by the receiver 24 of FIG. 4, 32 denotes the variable part of the absorbed radiations due to the pulsating or oscillating progress of the perturbation transmitted through the needle 17 (the undulating component of pressure and/or flow in the arterial blood), 33 denotes the part (substantially constant in time) of the radiations due to the absorption of the venous blood, 34 the part (substantially constant in time) of radiation due to the absorption of the venous blood, 35 the part (substantially constant) due to the absorption of other tissues (bone, skin, muscles etc). FIG. 7 illustrates the same graph as in FIG. 6, in greater detail. The graph is substantially of the reflective type rather than of the absorption type.

In general, the monitoring apparatus of the invention comprises a fluid transport system for moving a fluid. The fluid can be, for example, a medical fluid—such as for example a medication, a buffer solution or an anticoagulant in an extracorporeal blood treatment, a replacement fluid in a hemo(dia)filtration treatment—or a corporeal fluid, such as for example the blood removed to be treated in an extracorporeal treatment device and/or the blood returned after the treatment. This fluid transport system can comprise, for example, an infusion circuit in the vascular system of a patient, a circuit for processing blood from a donor, a circuit for an extracorporeal blood treatment of a patient, an extracorporeal blood circuit for treatment of kidney failure and/or hepatic insufficiency (for example a blood circuit for dialysis, hemo(dia)filtration, pure ultrafiltration, therapeutic plasma exchange, hemoperfusion, etc.). In particular the extracorporeal blood circuit of FIG. 2 can comprise any one of the known-type circuits used in hemodialysis, hemodiafiltration, hemofiltration and hemoperfusion treatments, in treatment of hepatic insufficiency, etc. In FIG. 2, for the sake of simplicity, the various elements with which a known circuit of the above-mentioned type is provided have not been illustrated.

The monitoring apparatus of the invention can comprise, as in the above examples, at least a needle connected to the fluid transport system and to a vascular access of an individual. The needle can be configured to introduce and/or remove a fluid into/from the vascular system of the individual. The vascular access can be of any kind of vascular access of known type. The connection between the fluid transport system and the vascular access can be a single-needle type (for example the system of FIG. 1 or even a single-needle dialysis system or another single-needle system for processing the extracorporeal blood) or a double-needle type. The fluid transport system and the vascular access are connected to one another and/or removed from the vascular access by passing through the above-mentioned needle or needles.

The monitoring apparatus of the invention can comprise, as in the above-mentioned examples, a perturbation generator configured for generating variations of at least a parameter (in particular a chemical/physical parameter of the fluid) in the above-cited fluid transport system and/or in the needle (or needles). The perturbation generator comprises, optionally, at least an actuator arranged in the fluid transport system. The perturbation generator optionally comprises at least an actuator arranged in the fluid transport system. The perturbation generator is optionally configured to generate variations of the parameter, of the pulsating or undulating type. The parameter can comprise one or more chemical/physical characteristics of the fluid.

The parameter can comprise, for example, one of the following fluid characteristics or a known function of one or more of these characteristics: pressure, flow (in volume or mass), temperature, viscosity, hematocrit, conductivity, concentration of a substance in the fluid, optical properties (for example reflections or absorption of the light), speed of propagation of the sound.

The perturbation generator can comprise, for example, a pressure and/or flow variation generator in the fluid transport system. The pressure and/or flow variation generator comprises, optionally, a flexible-wall deformation pump configured for fluid transport, such as for example a rotary-type peristaltic pump (as in FIG. 2), or any other type of pump used in the prior art for movement of fluids in the medical field which can generate variations (of a pulsating or undulating type) of pressure and/or flow. In the case of a peristaltic pump the generation of pressure and/or flow waves is determined by the normal functioning of the pump. In the specific case of FIG. 2, the perturbation generator is a blood pump (for example of the type used in a dialysis circuit).

Other types of perturbation generators can be used, as can other ways of generating the perturbations such as, for example, by means of oscillating variation of the set value of the fluid supply pump flow rate, and/or by means of the introduction (for example with an oscillating flow) of a second fluid (having at least a different characteristic, such as temperature, concentration, viscosity etc., with respect to the main fluid) into the main flow of the fluid transport system, and/or by means of removing (for example with an oscillating flow or a variable flow according to a prefixed regime) of a part of the fluid (for example the liquid part of a fluid also containing solid parts in suspension; reference in particular is made to a plasmatic liquid present in the blood which can be ultrafiltered through a sempermeable membrane, such as for example the membrane 9).

As has been seen, the monitoring apparatus of the invention comprises a sensor configured for application (direct or indirect) to the body of an individual. In the specific embodiment of FIG. 1, the sensor is applied to the skin of the individual. The sensor can optionally be of the type configured for direct application in contact with the body of the individual. In use, a determined perturbation (for example oscillatory) induced in a zone of the fluid transport system propagates along the system and reaches the vascular access zone. Here the perturbation passes through the needle and form here propagates, at least partially, internally of the body of the individual, in particular along a part of the vascular system, in particular at least the part which faces and is most closely interested by the fluid flow passing through the needle (entering or exiting from the extracorporeal fluid transport system). The perturbation, which originates in the extracorporeal system and which—passing through the needle—propagates within the body of the individual, can be detected by the sensor which is operatively associated to the individual's body. The sensor is configured to emit a signal indicating the above-mentioned variations of the parameter which are transmitted through the needle (or needles).

The sensor comprises at least an active part which can assume at least an operative configuration in which it interacts, for example contactingly, with the individual's body and in which it is not rigidly constrained to the needle. The active part of the sensor optionally constitutes an independent unit with respect to the needle. Overall the sensor too can constitute an independent unit with respect to the needle. The sensor can, in substance, form a structurally and functionally isolated unit with respect to the needle itself. By virtue of the structure and functionality of the sensor, the application of the sensor itself to the individual's body can be performed independently with respect to application of the needle. The two applications (of the needle and the sensor) to the patient can be done at different times, since the needle and the sensor form two distinct units. The connection between the two units consists, essentially, of the fact that the sensor is predisposed to receive a signal which, originating from the fluid transport system, can pass through the needle and a part of the tissues of the individual's body which, with the needle correctly positioned, are interposed between the needle and the sensor. The needle and the active part of the sensor are optionally not solidly constrained to one another, so that the movement of the needle does not necessarily lead to the movement of the sensor.

The needle has a proximal end which is configured to penetrate, in a known way, a vascular access, and a distal end which is connected, in a known way, to the fluid transport system. When the proximal end is in a normal operative configuration, in which it penetrates into the vascular access, the proximal end is optionally arranged in an intermediate zone between the distal end and the active part of the sensor (as illustrated in FIGS. 1, 2 and 3). In other words, the sensor is arranged such as to be operatively associated to the part of the body of the individual which is most greatly interested by the flow which exits from (or enters) the needle. Normally the needle, in the correct position, assumes an oblique orientation with respect to the surface of the body. The sensor can operate, in other words, on a zone of the surface of the body which is close to the needle and which forms, with the needle itself (which needle, as mentioned is in an oblique position), obtuse angles (such as in FIGS. 1 to 3). In this way the zone in which the sensor operates is the zone of the individual's body where the greater part of the fluid which passed or will pass through the needle flows. This enables the sensor to operate on a signal of greater intensity. It is however possible to have it so that the sensor is configured to operate in the zone of the body that forms an acute angle with the needle arranged obliquely, i.e. in other words with the sensor arranged substantially below the needle, i.e. "internally" of the extension and/or the straight prolongation of the oblique needle, out of the individual's body (and not "externally" to the extension and/or prolongation, as happens in the above-described case).

The active part of the sensor can optionally assume at least an operative configuration in which it interacts contactingly or nearly contactingly with a surface of the individual's body. The sensor can comprise a physiological sensor for detecting at least a physiological parameter of the individual. In a specific embodiment (as has already been seen) the sensor can comprise at least an emitter of radiation and a receiver of radation. The emitter and the receiver of radiation can be configured to be operatively associated to at least a tissue of the individual's body. The radiation emitter can comprise, for example, at least an emitter of light radiations. The emitter and the receiver of radiation are configured to be arranged on two opposite sides of the tissue and/or a same side of the tissue. The radiation receiver can comprise at least a receiver of radiations reflected from the tissue and/or at least a receiver of radiations absorbed by the tissue. It is however possible to include the use of a plurality of sensors, which can be different from each other.

In the embodiment illustrated in the accompanying figures of the drawings, in particular FIGS. 2 to 5, the sensor can comprise a pulsimeter, such as for example a finger pulsimeter or a frontal pulsimeter. A pulse oximetry sensor is configured, as is known, to perform a trans-illumination of a portion of the body crossed by the blood and to measure the extinction of the light (due to reflection and/or absorption) during the trans-illumination. The sensor can be mounted on a finger, in particular a finger-tip, or on other parts of the body (arm, leg etc.), in proximity of the vascular access. In particular the sensor is mounted, optionally, such as to trans-illuminate a portion of the body crossed by the blood just returned through the venous needle (or just before entering the arterial needle). As is known, a pulse oximeter is able to provide a progress chart of the vascular pulsation (pletismographic curve, see FIG. 7), as well as other data, such as cardiac frequency, oxygen saturation and perfusion index.

Other types of sensors can be used, such as for example an intracorporeal blood pressure sensor, of a type which measures the systolic pressure of the individual and/or the diastolic pressure and/or the mean arterial pressure. It is further possible to use a temperature sensor, a viscosity sensor, a hematocrit sensor, a conductivity sensor, a substance or element concentration sensor or a sensor of a type of particle, an ultrasound sensor (or other type of acoustic sensor), an infrared sensor (or other type of optical sensor), etc.

The monitoring apparatus comprises an analysis device for recognising the detachment of the at least a needle on the basis of the signal. The analysis device is configured for discriminating, in the signal provided by the sensor, the above-mentioned variations of the parameter transmitted through the vascular access, and for comparing the transmitted variations with at least a threshold value. The analysis device can comprise, for example, at least a filter for processing the signal emitted by the sensor such as to identify the above-mentioned variations passed through the vascular access. In particular the analysis device is programmed to identify, in the signal provided by the sensor, the component of the signal which is due to the pulsating or oscillating progress of the perturbation.

In a further embodiment, the perturbation generator 5 can comprise a sound energy generator (for example an ultrasound generator), and the sensor 6 can comprise an acoustic sensor configured for detecting the above-mentioned sound energy. The perturbation generator 5, in this as in the preceding cases, can be configured to generate an isolated pulsation (a momentary change in a determined parameter), such as for example a sound pulse, or in order to generate variations of a pulsating type of at least a parameter, such as for example periodical oscillating or undulating variations of a determined parameter, for example a sound wave, or for generating a series of pulsations with a determined frequency or period.

The invention claimed is:

1. An apparatus for monitoring a vascular access, comprising:
    a fluid transport system for moving a fluid;
    at least one needle connected to the fluid transport system and to a vascular access of an individual, the needle being configured to supply the fluid to the vascular access, to remove the fluid from the vascular access, or to both supply the fluid to the vascular access and to remove the fluid from the vascular access;
    a perturbation generator configured to generate variations of at least one parameter in the fluid transport system, to generate variations of at least one parameter in the needle, or to generate variations of at least one parameter in both the fluid transport system and in the needle;
    a sensor configured to be applied directly to the individuals body independent of the needle and the fluid transport system,
    wherein the sensor comprises at least an emitter of light radiation and a receiver of light radiation configured to emit a signal indicating the variations of at least one parameter generated by the perturbation generator and transmitted through the needle, the emitter of light radiations and the receiver of light radiations configured to be operatively associated to at least a tissue of the individual's body; and
    an analysis device configured to recognize a detachment of the at least one needle, on a basis of said signal.

2. The apparatus of claim 1, wherein the perturbation generator is operatively directly associated to the fluid transport system.

3. The apparatus of claim 1, wherein the perturbation generator comprises at least an actuator arranged in the fluid transport system.

4. The apparatus of claim 1, wherein the fluid transport system comprises at least an actuator, the perturbation generator comprising the actuator.

5. The apparatus of claim 1, wherein the sensor comprises at least an active part configured to assume at least an operative configuration in which the sensor interacts with the individual's body and is not constrained rigidly to the needle.

6. The apparatus of claim 1, wherein:
    the at least one needle has a proximal end configured to penetrate a vascular access at a point of penetration and a distal end connected to the fluid transport system;
    the sensor comprises at least an active part configured to assume at least an operative configuration in which the sensor interacts with the individual's body such that, when the proximal end is in a normal operative configuration in which the proximal end penetrates into the vascular access, said point of penetration is arranged in an intermediate zone between the distal end and the active part.

7. The apparatus of claim 1, wherein the sensor comprises at least an active part configured to assume at least an operative configuration in which the active part interacts contactingly or nearly contactingly with a surface of the individual's body.

8. The apparatus of claim 1, wherein the sensor comprises a physiological sensor for detecting at least a physiological parameter of the individual.

9. The apparatus of claim 1, wherein the emitter of light radiation and the receiver of light radiation are configured to be arranged on first and second opposite sides of the tissue.

10. The apparatus of claim 1 wherein the emitter of light radiation and the receiver of light radiation are configured to be arranged on a same side of the tissue.

11. The apparatus of claim 1, wherein the receiver of light radiation comprises at least a receiver of light radiation reflected by the tissue or at least a receiver of light radiations absorbed by the tissue.

12. The apparatus of claim 1, wherein the sensor comprises one or more sensors selected from the group of sensors including: a pulsimeter, an intracorporeal blood pressure sensor, an acoustic sensor, and an optic sensor.

13. The apparatus of claim 12, wherein the pulsimeter comprises a finger pulsimeter.

14. The apparatus of claim 12 or 13, wherein the intracorporeal blood pressure sensor is configured to measure at least one of a systolic pressure of the individual, a diastolic pressure of the individual, or the mean arterial pressure of the individual.

15. The apparatus of claim 1, wherein the analysis device is configured to discriminate, in the signal provided by the sensor, the variation of at least one parameter transmitted through the vascular access, and to compare the variation with at least one threshold value.

16. The apparatus of claim 1, wherein the analysis device comprises at least a filter for processing the signal emitted by the sensor, said filter configured to identify the variations of at least one parameter transmitted through the vascular access.

17. The apparatus of claim 1, wherein the fluid transport system comprises an extracorporeal blood circuit configured to remove blood from and return blood to the individual's body, the needle being a blood return needle.

18. The apparatus of claim 17, wherein the fluid transport system comprises a membrane exchanger having a blood chamber and a fluid chamber separated from one another by a semipermeable membrane, the extracorporeal blood circuit having a blood removal line connected to an inlet of the blood chamber and a blood return line connected to an exit of the blood chamber.

19. The apparatus of claim 1, wherein the perturbation generator is configured to generate pulsating-type variations of the at least one parameter.

20. The apparatus of claim 1, wherein the perturbation generator is operatively associated in contact with a flexible wall delimiting a fluid path of the fluid transport system.

21. The apparatus of claim 1, wherein the at least one parameter comprises at least one parameter of the fluid selected from a group comprising: pressure, flow, temperature, viscosity, hematocrit, conductivity, concentration of a substance in the fluid, optical properties, optical absorption, optical reflection, acoustic properties, acoustic impedance, and velocity of sound propagation.

22. The apparatus of claim 1, wherein the perturbation generator comprises at least a generator of variations of pressure, flow, or both pressure and flow in the fluid transport system.

23. The apparatus of claim 22, wherein the generator of variations of pressure, flow, or both pressure and flow comprises a flexible-wall deformation pump configured for fluid transport.

24. The apparatus of claim 23, wherein the flexible-wall deformation pump comprises a peristaltic pump.

25. The apparatus of claim 23, wherein the flexible-wall deformation pump is a rotary pump.

26. A method for monitoring a vascular access, comprising:
providing a fluid transport system;
connecting at least one needle to the fluid transport system and to a vascular access of an individual;
supplying, removing, or supplying and removing a fluid to the vascular access, from the vascular access, or to and from the vascular access through the at least one needle;
generating variations of at least one parameter in the fluid transport system, generating variations of at least one parameter in the at least one needle, or generating variations of at least one parameter in both the fluid transport system and in the at least one needle;
applying a sensor directly to the individual's body independent of the needle and the fluid transport system, wherein the sensor comprises at least an emitter of light radiation and a receiver of light radiation configured to emit a signal indicating the variations of at least one parameter generated by the perturbation generator and transmitted through the needle, the emitter of light radiations and the receiver of light radiations configured to be operatively associated to at least a tissue of the individual's body;
monitoring the individual's body in order to identify the signal indicating the variations of at least one parameter transmitted through the at least one needle; and
recognising a detachment of the at least one needle on a basis of the monitoring.

27. The method of claim 26, wherein the variations of at least one parameter are generated directly in the fluid transport system.

28. The method of claim 26, further comprising connecting an actuator to the fluid transport system, the variation of at least one parameter being generated by the actuator.

29. The method of claim 26, wherein the variations of at least one parameter are generated by an actuator of the fluid transport system.

30. The method of claim 26, further comprising stages of positioning a sensor for the monitoring on the individual's body, and positioning the at least one needle on the individual's body, the positioning stages being performed independently from one another.

31. The method of claim 26, wherein:
the at least one needle has a proximal end configured to penetrate a vascular access and a distal end connected to the fluid transport system;
the method further comprising a stage of positioning a sensor for monitoring on the individual's body such that when the proximal end is in a normal operating configuration in which the proximal end is penetrating the vascular access, the proximal end is arranged in an intermediate zone between the distal end and an active part of the sensor which interacts with the individual's body.

32. The method of claim 26, further comprising a stage of positioning a sensor for monitoring such that the sensor has an active part which interacts in contact or nearly in contact with a surface of the individual's body.

33. The method of claim 26, wherein the stage of monitoring comprises detecting at least a physiological parameter of the individual.

34. The method of claim 26, wherein the stage of monitoring comprises at least an emission of light radiation on at least a tissue of the individual's body, and at least a receiving of the light radiation.

35. The method of claim 34, wherein the emission and reception of light radiation are performed on first and second opposite sides of the tissue.

36. The method of claim 34, wherein the emission and reception of light radiation are performed on a same side of the tissue.

37. The method of claim 34, wherein the light radiation received comprises reflected light radiation from the tissue, light radiation absorbed by the tissue, or light radiation reflected from and absorbed by the tissue.

38. The method of claim 26, wherein the monitoring comprises measuring at least one of pulse oximetry, intracorporeal blood pressure, an acoustic characteristic, or an optical characteristic.

39. The method of claim 38, wherein the pulse oximetry is measured at a finger of the individual.

40. The method of claim 38, wherein the intracorporeal blood pressure comprises at least one of a systolic pressure, a diastolic pressure, or a mean arterial pressure of the individual.

41. The method of claim 26, wherein the stage of recognising the detachment of the needle comprises:
detecting a signal indicating a characteristic of the individual's body;

discriminating, in the signal, a part due to the variation of at least one parameter transmitted through the vascular access; and comparing the variation with at least one threshold value.

42. The method of claim 26, comprising at least a filtering stage for processing a signal indicating a characteristic of the individual's body such as to identify, in the signal, the part thereof which is due to the variation of at least one parameter transmitted through the vascular access.

43. The method of claim 26, wherein the fluid transport system comprises an extracorporeal blood circuit configured for removing and returning blood from and to the individual's body, the needle being a blood return needle.

44. The method of claim 43, wherein the fluid transport system comprises a membrane exchanger having a blood chamber and a fluid chamber separated from one another by a semipermeable membrane, the extracorporeal blood circuit having a blood removal line connected to an inlet of the blood chamber and a blood return line connected to an outlet of the blood chamber.

45. The method of claim 26, wherein the variation of at least one parameter comprises a variation of the parameter of a pulsating type.

46. The method of claim 26, comprising a stage of connecting a perturbation generator contactingly with a flexible wall delimiting a fluid path in the fluid transport system, the variation of at least one parameter being generated by the perturbation generator.

47. The method of claim 26, wherein the at least one parameter comprises at least one parameter of the fluid selected from a group comprising: pressure, flow, temperature, viscosity, hematocrit, conductivity, concentration of a substance in the fluid, optical properties, optical absorption, optical reflection, acoustic properties, acoustic impedance, and velocity of sound propagation.

48. The method of claim 26, wherein the stage of generating variations of at least one parameter comprises varying pressure, flow, or both pressure and flow in the fluid transport system.

49. The method of claim 48, wherein the stage of generating variations of at least one parameter comprises activating a flexible-wall deformation pump configured for fluid transport.

50. The method of claim 49, wherein the flexible-wall deformation pump comprises a peristaltic pump.

51. The method of claim 48 or 49, wherein the flexible-wall deformation pump is a rotary pump.

* * * * *